(12) United States Patent
Wien (10) Patent No.: US 8,132,579 B1
(45) Date of Patent: Mar. 13, 2012

(54) DENTAL FLOSS DEVICE

(76) Inventor: Abraham Wien, Miami, FL (US)

( * ) Notice: Subject to any disclaimer, the term of this patent is extended or adjusted under 35 U.S.C. 154(b) by 34 days.

(21) Appl. No.: 12/761,369

(22) Filed: Apr. 15, 2010

(51) Int. Cl.
*A61C 15/00* (2006.01)

(52) U.S. Cl. ........................... 132/321; 132/329

(58) Field of Classification Search .................. 132/321, 132/329; D28/65
See application file for complete search history.

(56) References Cited

U.S. PATENT DOCUMENTS

| | | | | |
|---|---|---|---|---|
| 410,794 | A | * | 9/1889 | Hellwig ........................ 132/321 |
| 3,896,824 | A | | 7/1975 | Thornton |
| 3,943,949 | A | * | 3/1976 | Ashton et al. ................. 132/321 |
| 4,008,727 | A | * | 2/1977 | Thornton ....................... 132/321 |
| 4,142,538 | A | * | 3/1979 | Thornton ....................... 132/321 |
| 4,265,258 | A | * | 5/1981 | Eaton, II ....................... 132/321 |
| 4,277,297 | A | | 7/1981 | Thornton |
| 4,974,615 | A | * | 12/1990 | Doundoulakis ............... 132/321 |
| 4,986,288 | A | | 1/1991 | Kent |
| 5,063,948 | A | * | 11/1991 | Lloyd ............................ 132/321 |
| 5,280,796 | A | * | 1/1994 | Rosenberger ................. 132/321 |
| 5,311,890 | A | * | 5/1994 | Thornton ....................... 132/329 |
| 5,316,028 | A | * | 5/1994 | Flemming ..................... 132/329 |
| 5,423,337 | A | * | 6/1995 | Ahlert et al. .................. 132/321 |
| 5,433,226 | A | * | 7/1995 | Burch ............................ 132/321 |
| 5,505,216 | A | * | 4/1996 | Gilligan et al. ............... 132/321 |
| 5,545,480 | A | * | 8/1996 | Lalani ............................ 428/364 |
| 5,566,691 | A | * | 10/1996 | Dolan et al. ................... 132/321 |
| 5,682,911 | A | * | 11/1997 | Harada .......................... 132/321 |
| 5,692,530 | A | * | 12/1997 | Bible et al. .................... 132/321 |
| 5,851,116 | A | | 12/1998 | Margolis |
| 5,857,471 | A | * | 1/1999 | Harada .......................... 132/321 |
| 6,152,147 | A | | 11/2000 | Sanchez |
| 6,250,313 | B1 | * | 6/2001 | Rees .............................. 132/321 |
| 6,453,912 | B1 | | 9/2002 | Antler |
| 6,672,316 | B1 | * | 1/2004 | Weihrauch ..................... 132/321 |
| 6,814,085 | B2 | | 11/2004 | Brattesani |
| 7,281,541 | B2 | | 10/2007 | Lorch |
| 7,487,785 | B2 | | 2/2009 | Dougan |
| 2001/0029962 | A1 | * | 10/2001 | Bergman et al. .............. 132/200 |
| 2003/0154998 | A1 | * | 8/2003 | Falleiros et al. .............. 132/321 |

(Continued)

FOREIGN PATENT DOCUMENTS

EP 764431 A2 3/1997

*Primary Examiner* — Rachel Steitz
*Assistant Examiner* — Tatiana Nobrega
(74) *Attorney, Agent, or Firm* — KB Patents; Luca D'Ottone (57) ABSTRACT

A dental hygiene device for cleaning, flossing, brushing, massaging the space between the teeth, crowns, and under the gumline includes a combination of a first portion of flexible filament floss to convey flexibility and strength to the filament and a second portion having a thicker and oblong shape where in some preferred embodiments bristles depart from the center of said filament floss. The second portion gradually slopes from the thickness of floss up to its maximum radius approximately located in the center, then gradually down-sloping from the maximum radius in the center down to the radius of floss where the second portion is designed to provide a brushing, cleaning, gum massaging means coupled with the floss. When used said first portion allows insertion in the interdental space especially in more difficult places such as between molars or crown and it can be used as regular dental floss to massage the gums and clean said spaces. The second portion has the principal function of brushing and cleaning the interdental space and massaging the gums. The primary function of said second portion is to deliver the cleaning action in spaces that are other wise difficult to reach such as in between molars, crowns, bleeding gingivas, dental prostheses, and so on by the way of being pulled and pushed forth and back by the user.

12 Claims, 7 Drawing Sheets

U.S. PATENT DOCUMENTS

| | | |
|---|---|---|
| 2004/0168703 A1 | 9/2004 | Cho |
| 2005/0279377 A1* | 12/2005 | Sarjeant ................. 132/321 |
| 2005/0279378 A1* | 12/2005 | Lorch ..................... 132/321 |
| 2006/0289032 A1* | 12/2006 | Satary-Ravabakhsh ...... 132/321 |
| 2007/0144553 A1* | 6/2007 | Hubbard ................. 132/321 |
| 2008/0314406 A1* | 12/2008 | Barrie .................... 132/329 |
| 2009/0120454 A1* | 5/2009 | Ochs et al. .............. 132/325 |
| 2011/0229849 A1* | 9/2011 | Maurer et al. ........... 433/136 |

* cited by examiner

DENTAL FLOSS DEVICE

FIELD OF THE INVENTION

The present invention relates to dental hygiene devices which are especially useful for cleaning, flossing, brushing, those portions of teeth, crowns, dental prosthesis, or orthodontic work lying in between neighboring teeth and for massaging the gums. More particularly the present invention relates to dental hygiene devices having two portions, a first portion and a second portion, alternatively assembled to constitute a longer dental cleaning filament portions which includes both a floss and a brush portions in one single device. Said first portion being a flexible filament floss, said second portion being thicker, and tougher to be used to deliver the brushing, cleaning, and massaging action.

BACKGROUND OF THE INVENTION

Regular dental checkups and periodic professional cleaning of the teeth to remove plaque are very important for good health, in addition to that a regular personal regimen of dental hygiene is essential to maintaining the health and appearance of the teeth and gums. The use of a manual toothbrush having an array of bristles mounted near one end of some form of handle is the most familiar and commonly-used implement for this purpose. It is estimated that about all American brush their teeth at least once a day. In contrast to that only a smaller percentage of the population in the range between 10 and 40% uses dental floss to complement the tooth-brushing with an additional cleaning or gum massaging action. The bristles of the prior art devices are not able to brush deep inside the gums between teeth especially in spaces that are difficult to reach such as in between the molars, close to crowns and bleeding gums.

Regular filament floss are very well know in the art and come in different varieties made either in nylon, silk, or biodegradable polymers. Prior art filaments can also be waxed, or not waxed, flavored, or not flavored, and in some instance disinfecting and cleaning composition are added to the filaments to make them more effective in their cleaning action. Usually prior art dental flosses are commercially available in packages or rolls of 10-50 meters of flexible uninterrupted filament that have a diameter within 0.003 and 1 [mm].

If compared with the brushing action of a toothbrush dental floss have the flexibility to be slided in the space in between the teeth removing food particles in a space that it is not otherwise accessible to a regular toothbrush. The downside of a dental floss with respect of a more conventional brushing apparatus is the fact that it comes just as a filament so does not have any brushing capacity whatsoever.

To overcome this deficiency of prior art dental floss inter-dental brushes have been developed. Nowadays most periodontologists prefer the use of inter-dental brushes rather than the use of the prior art dental floss because of the lack of brushing capacity of the first one. Inter-dental brushes though are made by plurality of bristles radially projecting from the center of a rigid structure often made by metal or plastic. Said rigid structure may puncture the gums causing bleedings, and its routinary use may in turn weaken the gums around the teeth causing gingivitis and gum disease.

In addition to what discussed so far U.S. Pat. No. 5,311,890 to Thornton discloses and claims a teeth cleaning element containing threading end portions for cleaning relatively large spaces in the teeth consists of from about 400 to about 800 filaments in an elongated bundle that is from about 1,200 to 2,400 about denier. Under the teachings of the Thornton patent said filaments at the mid-portion of the length of the bundle are textured with the crimps and crinkles of the texturing of the several filaments being intermingled and in contact at numerous points and being adhered together at the contact points to form a bulky, longitudinal, longitudinally and laterally resilient mass.

In the Thornton patent, the cleaning part of this dental devise is not an integral part of the filament, so that there are two distinct elements that are assembled together weakening the mechanical strength and resistant of the combination. Additionally under the Thornton patent the bulky, cleaning section is composed of crimps and crinkles of filaments made of synthetics resign that are put together by some sort of adhesive nylon resin. Thus a device assembled under Thornton, may become dangerous if the adhesive resin comes apart and gets stuck between the teeth and inside the gums.

U.S. Pat. No. 5,857,471 to Harada discloses and claims a dental hygiene device for cleaning enlarged embrasures includes a brush portion having a plurality of bristles projecting from a rigid spine opposed ends of which are secured to lengths of flexible filament such as dental floss. Under the teachings of the Harnada patent said free end of at least one of the filaments may be provided with a stiff pin-like tip useful as a toothpick or in threading the device through gaps between teeth or orthodontic structures.

The Harada patent discloses a device that is not flexible and it is rigid in nature with a stiff pin-like tip. Also in this patent, the brush part of this dental devise is not an integral part of the filament since two distinct elements are put together by several means of attachments, causing in turn potential limitation for harm such as the one described in the Thornton patent.

U.S. Pat. No. 5,063,948 to Lloyd discloses and claims a bristled dental floss comprised of a plurality of sub-fibers each having a plurality of bristles secured thereto. Under the teachings of the Lloyd patent said sub-fibers, bristles, or both, may be stiffened with wax, TEFLON, nylon, or like material. The Lloyd patent fails to disclose a flexible assembly as well. In fact Lloyd suggests the use of Wax, Teflon or Nylon material to enhance the rigid character of its device. Also in the Lloyd patent the bristles or brushing, cleaning parts are not an integral part of the filament causing in turn potential limitation for harm such as the one described in the Thornton patent.

The prior art solutions hence are not entirely sufficient to effectively clean all areas especially those adjacent spaces or gaps such as those present between teeth, especially when root surfaces are exposed without causing damage to the gums.

SUMMARY OF THE INVENTION

In view of the limitations of the prior art described above, it is an object of the invention to provide a flexible dental filament floss and gum massage device which cannot only be used as a dental floss but which can be used to clean the space in between the teeth, crowns, roots, gingiva, and under and around dental prothesis, and orthodontic structures adjacent enlarged embrasures with efficacy comparable to that of an inter-dental brush but without the potential for harm and bleeding of the gums associated with the rigid and stiff structure of an inter-dental brush.

It is then another objective of the present invention to provide for a flexible dental filament floss that combine the flexibility of a dental floss associated with the brushing efficiency of an inter-dental brush. In other words the device of the present invention combines the flexibility of a dental floss with the ability to brush the interdental space that only specialized devices currently on the market have in a simple, and easy to use device.

It is then an additional objective of the present invention a flexible dental filament floss to provide gum massage to stimulate and promote gum's health.

It is a further object of the present invention to provide for a flexible dental filament floss which can be manufactured and sold at low cost. In one of the preferred embodiments the novel dental cleaning filament is made in pre cut sections for easy of use (or) as a long filament that could be cut at any length by the user.

The present invention meets the foregoing objectives by providing a novel and improved flexible dental filament floss which includes a combination of two portions, a first portion and a second portion, alternatively assembled to constitute a longer floss. Said first portion being a flexible filament floss, said second portion having the function to brush, clean, massage, the surfaces in the interdental spaces.

This second portion may be embodied in various generally oblong shapes being thinner at the junction with said first portion and generally thicker in its mid point. Both portions are disclosed to be an integral part of the overall structure. This unitary structure provides for a portion that can be inserted between the teeth and act as a floss with all the function related and for a portion that can be slide forth and back in the interdental space to brush, clean, and massage said space.

Unlike prior art devices in which bristles project from a rigid portion of the filament, the invention contemplates a generally oblong shape that presents various embodiments including abut not limited to a coated oblong lump or a housing said for radially departing bristles and a thicker and tougher portion of various materials.

These and other objects and advantages of the present invention will become even more clear to persons of ordinary skill in light of the following detailed description and the appended drawings in which like reference numerals designate like items.

DETAILED DESCRIPTION OF THE INVENTION

Figure 1:
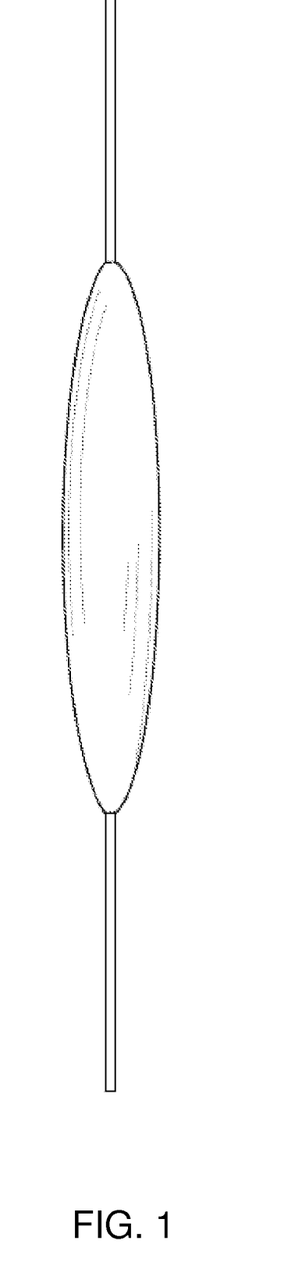
FIG. 1 is a lateral view of one of the preferred embodiments of the flexible dental filament floss built in accordance with the teachings of the present application.
Figure 7:
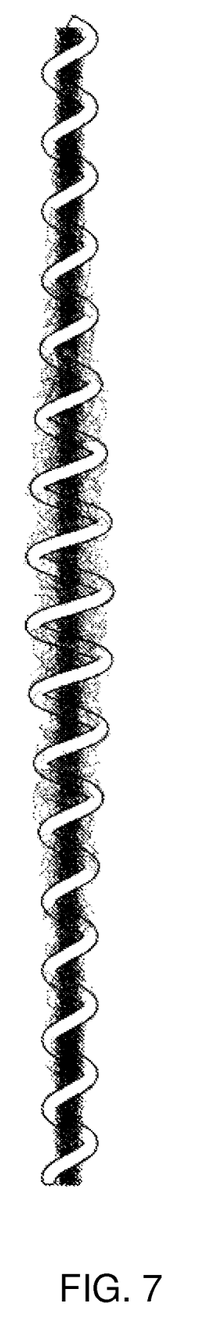
FIG. 7 is a lateral view of a second preferred embodiments of the flexible dental filament floss built in accordance with the teachings of the present application.
Figure 8:
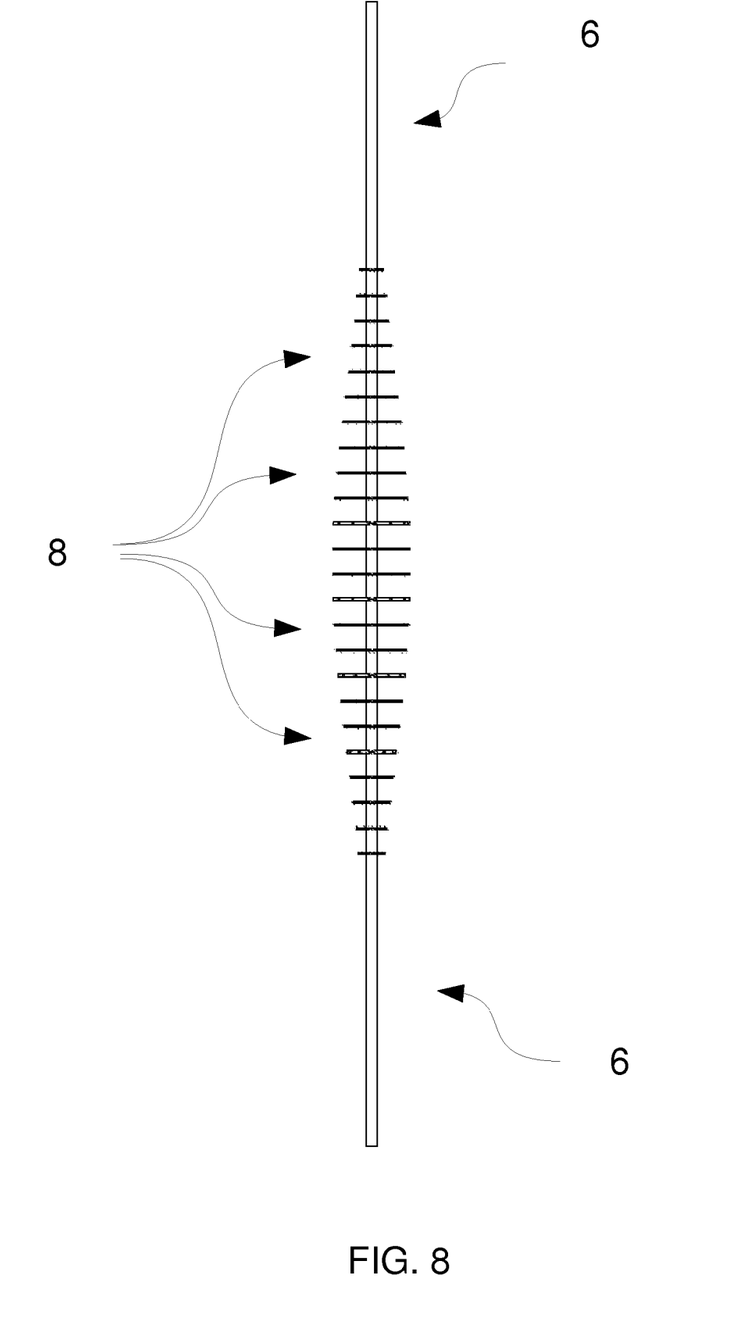
FIG. 8 is a lateral view of one of a third preferred embodiments of the flexible dental filament floss built in accordance with the teachings of the present application.

With reference to the drawings the novel flexible dental filament floss of the present invention is represented in three preferred embodiments: a first, a second, and a third preferred embodiment respectively illustrated in FIG. 1, FIG. 7, and FIG. 8. The order of these embodiments it is not important and does not represent their relative importance. Other embodiments may be manufactured and produced in accordance to the teachings of the present application.

The general aspect of the device of the present invention is represented in FIGS. 1-8. All the embodiments in FIGS. 1-8 feature an alternating pattern of thicker (2) and smaller portions (1) integrally constituting the flexible dental filament floss herein described. As shown in FIG. 1 the thicker portion (2) has an oblong shape, slowly increasing its radial diameter from the point of conjunction with the first flexible portion of the floss all the way to reach its maximum (3) at the mid point of its lateral width then gradually decreasing. The drawings generally depict the device of the present invention as a flexible dental floss, comprising two alternating portions a first portion and a second portion said two portions continuously assembled together to constitute a self supporting strand.

In the embodiment of FIGS. 1-8 said first and second portion alternate indefinitely for the length of the whole flexible dental filament floss.

FIG. 1 represents one of the preferred embodiments of the present invention where a regular floss portion is alternated to an oblong lump portion of the same or similar material including but not limited to rubber, plastic, cotton, silk, starch, polymeric chains, or other. Under the teachings of the present invention said lump can be coated with various materials including but not limited to waxes, antibacterial, anti-inflammatory, antiseptic, cooling and refreshing compounds, and other compounds used for regular dental care.

Figure 2:
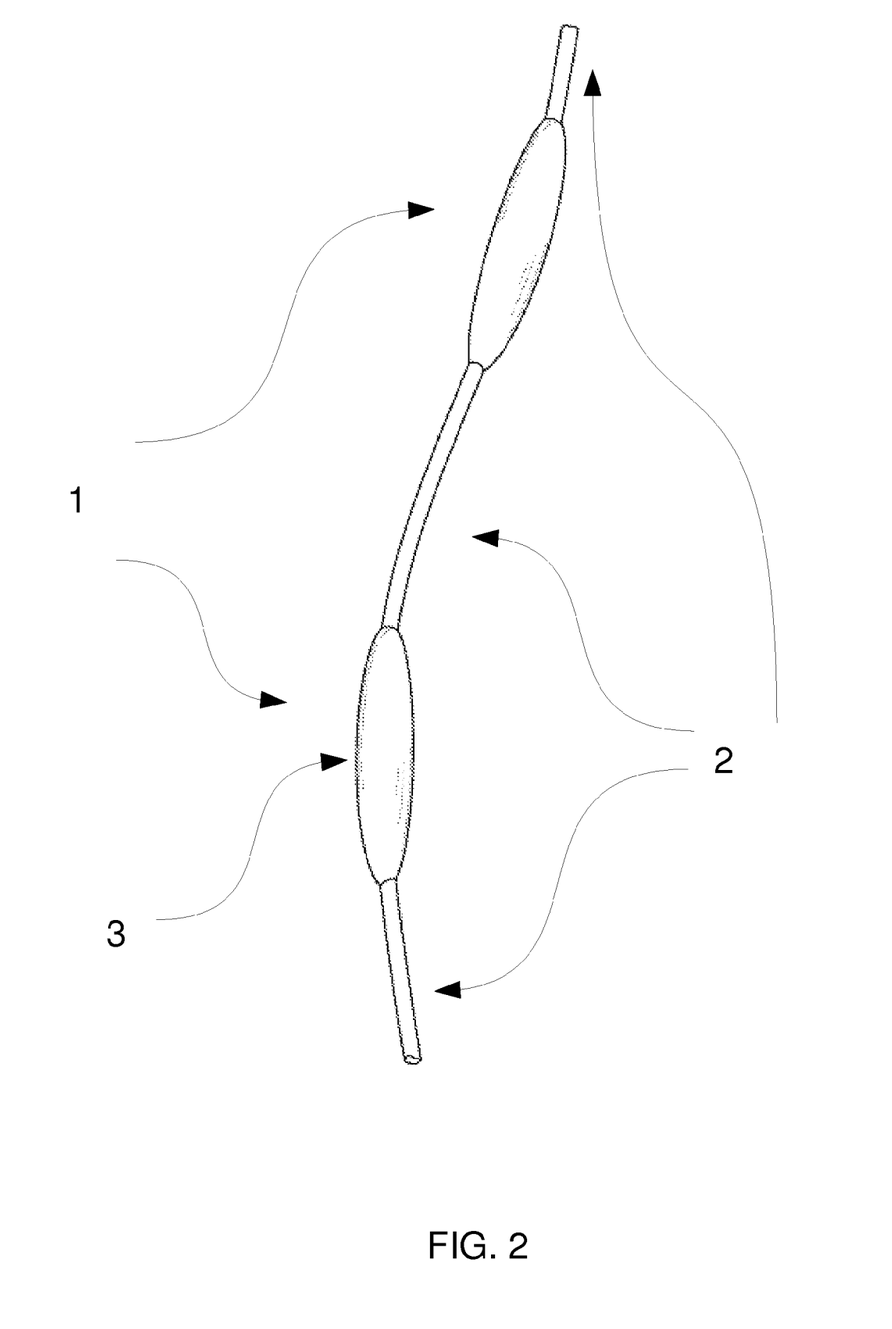
FIG. 2 is a lateral side view of a the first preferred embodiment of the flexible dental filament floss of FIG. 1.

FIG. 2 represents a first preferred embodiment. In the first preferred embodiment represented in FIG. 2 an elongate lump (2) is formed around the floss (1) of the same or different material, in the alternate mode described above.

Figure 3:
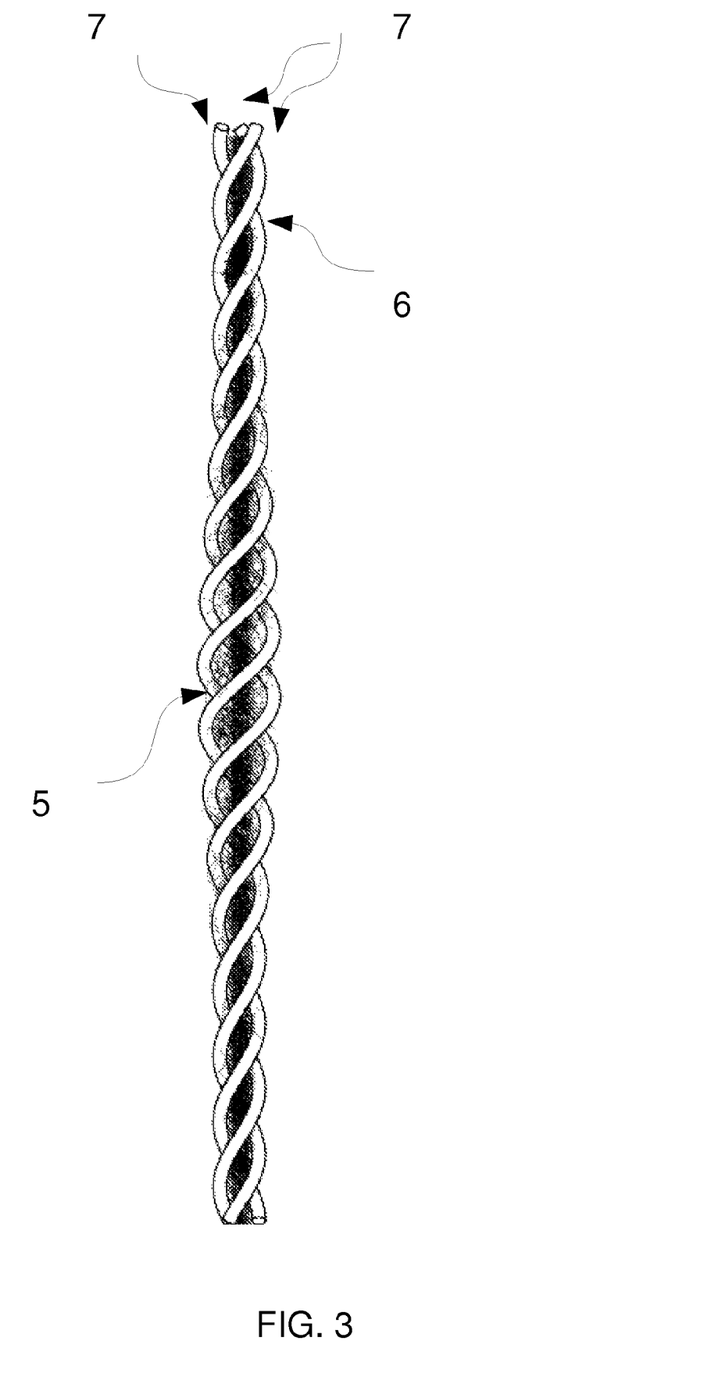
FIG. 3 is a lateral side view of the second preferred embodiment of the flexible dental filament floss of FIG. 7 showing the detail of the external structure.

FIG. 3 represents a second preferred embodiment of the flexible dental filament floss of the present application. In this embodiment a fluffy material (5) surrounds the central flexible floss (6) and it is tied down by a combination of three or more stronger, flat, outside filaments (7) twisted around it.

Figure 4:
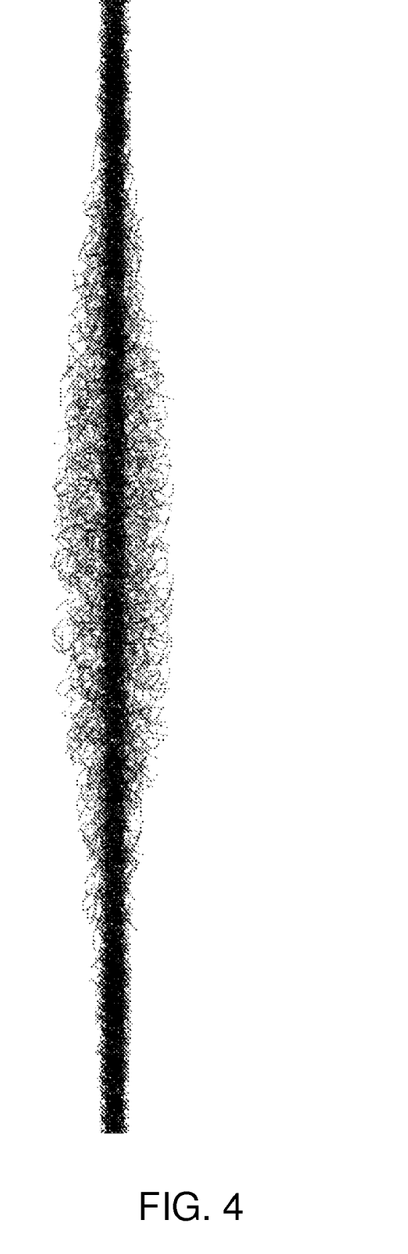
FIG. 4 is a lateral side view of the second preferred embodiment of the flexible dental filament floss of FIG. 7 showing the detail of the internal structure.
Figure 5:
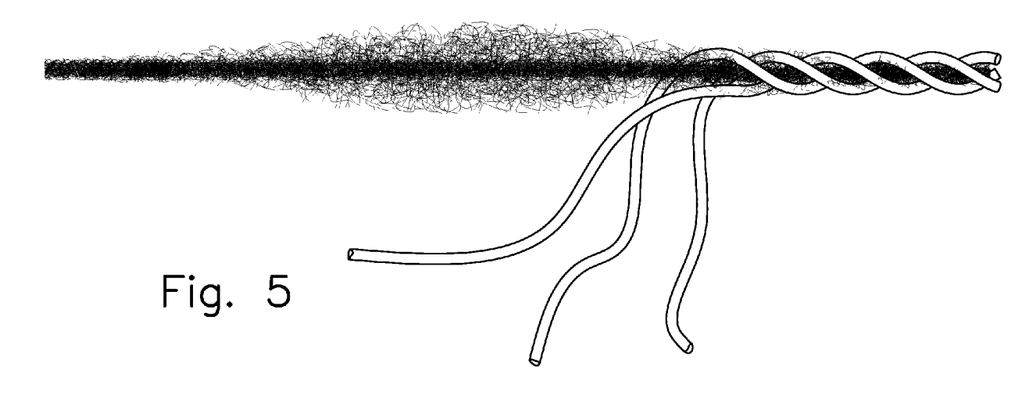
FIG. 5 is a lateral side view of the second preferred embodiment of the flexible dental filament floss of FIG. 7 showing during the making.
Figure 6:
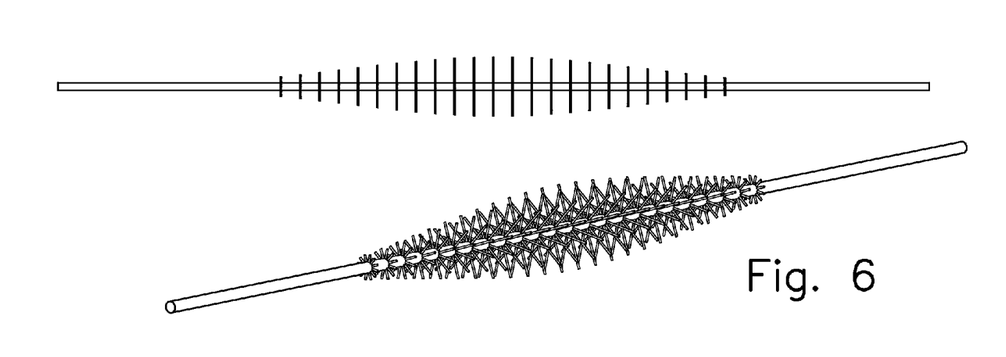
FIG. 6 is a lateral side view of a the third preferred embodiment of the flexible dental filament floss s of FIG. 8.

FIG. 4 represents the details of the internal flexible floss surrounded by the fluffy material, and FIG. 5 represents a detail of the process to manufacture this second preferred embodiment where the three outside flat filaments are being twisted in a braided fashion but have not yet reached the fluffy central portion. The embodiment of FIG. 5 represents a filament floss under the teachings of the present invention where said outside layer consist of three separate filaments braided together to form an involving twist only as an example. Other preferred embodiments include one or more filaments.

It is important to notice that while the outside filaments are twisted and braided all around the fluffy material, in turn trapping it, there are still sufficient spaces in between them for the fluffy, and spongy portions of the material spread out, thus improving the brushing and massaging functions. With this embodiment in fact the brushing, cleaning, and massaging action is due to a combination of the outside surface of the three outside filaments and of the portions of the spongy material entrapped in the twisted filaments that can still spring out of the plait.

With reference to FIG. 8 said second filament has a plurality of bristles departing from its base interior side and extruding toward the outside, these bristles are also referred as the hairs of said second filament. As shown in FIG. 8 two lighter filaments can be molded into said first stronger filament in diametrically opposed positions so to have a full radial coverage of said first filament and in turn to cover with their hairs the whole surface of said first filament on said second hairy portion.

As disclosed in the previous paragraphs of the present application the hairy portion of the filament alternates with straight simple filament portions used to hold the filament and or to slide it in between the teeth in a backward and forward motion. The distance between repeating set of bristles of between the hairy and the simple filament portions may vary depending on the biometrics of the target population to which the device is to be marketed.

A second preferred embodiment of the present invention teaches a first stronger filament and a second lighter and haired filament. Said second haired filament has alternating portions respectively either flat or hairy. The hairy portion of said second lighter filament can either have hairs on one side only or on radially departing from the center of the cross section of that filament in all directions.

In the second preferred embodiment of the present invention the claimed flexible dental filament floss is assembled by spiraling said second hairy lighter filament around a first stronger filament not shown in the drawings. The resulting creates a random radial distribution of said bristles all around the stronger central filament.

Depending on the process used and on the kind of hairy filament employed, and on whether the hairs or bristles departs from only one side or from both sides the resulting outcome of the novel dental floss of the present invention may either have hairy on both sides or only on one.

Either embodiment can be organized as a round dental floss or in individually cut pieces sufficient for the daily operations of dental hygiene. Either embodiment can be manufactured with various kind of material, and corroborated with waxes, antibacterial solutions, refreshing compounds, or blood stopping or cauterizing compounds already known in the art.

To fully describe the unique characteristics of the novel floss brush of the present invention one must refer to the method it can be used. The user can slide the filament portion between the teeth because of its smaller diameter and floss the inter-dental space with the floss portion of the filament. When needed, the user can slide said second portion of the filament, also know and referred as the brush portion, for better cleaning, brushing, and massaging.

Using the invention object of the present application in the fashion described above overcome most of the deficiencies of the prior art enabling the user the flexibility to insert the floss using the filament portion of it and to massage and brush the gums and the inter-dental space once the filament is already in. The prior art devices in fact require the use of two or more different devices to achieve the objective of the device object of the present invention. Often these two devices are sold separately involving a higher price for the consumer and a higher manufacturing cost for the producer. Interdental brushes can also pierce the gums with their metal or plastic parts and are not as flexible as the thicker portion of the device of the present invention used to achieve their same goal.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

I claim:

1. A dental floss device comprising: a plurality of filaments assembled together forming an outside layer, a plurality of fluffy and spongy portions, arranged within said outside layer, said outside layer is wrapped around said fluffy and spongy portions to form a continuous strand characterized by two portions a first flexible thin portion and a second oblong shaped portion so that said oblong shaped portion gradually slopes from the thickness of said first flexible thin portion to a maximum radius located approximately at a center of the oblong shaped portion and gradually slopes down from its maximum radius to the radius of the first flexible thin portion.

2. The dental floss device of claim 1 where said plurality of filaments are braided together to form said outside layer.

3. The dental floss device of claim 1 where said plurality of filaments are twisted together to form said outside layer.

4. The dental floss device of claim 1 where said fluffy and spongy portions spread out through the holes formed in said outside layer.

5. The dental floss device of claim 1 where said filaments assembled together to form the outside layer are three separate filaments.

6. The dental floss of claim 1 where the filaments of said outside layer are made of starch.

7. The dental floss of claim 1 where said fluffy and spongy portions are made of starch.

8. The dental floss of claim 1 where said filaments of said outside layer are made of rubber, plastic, cotton, silk, or nylon.

9. The dental floss of claim 1 where said fluffy and spongy portions are made of rubber, plastic, cotton, silk, or nylon.

10. The dental floss of claim 1 where the filaments of said outside layer is coated with waxy material.

11. The dental floss of claim 1 where said fluffy and spongy portions are embedded with antibacterial solutions, refreshing compounds, or cauterizing compounds.

12. The dental floss device of claim 1 where said outside layer and said fluffy and spongy portions are arranged around a central flexible filament.

* * * * *